United States Patent [19]
O'Brien

[11] Patent Number: 5,435,723
[45] Date of Patent: Jul. 25, 1995

[54] ENDOSSEOUS DENTAL IMPLANT SYSTEM

[76] Inventor: Gary R. O'Brien, 909 Cavanagh Rd., Glendale, Calif. 91207

[21] Appl. No.: 108,869

[22] Filed: Aug. 18, 1993

[51] Int. Cl.⁶ .............................................. A61C 8/00
[52] U.S. Cl. .................................. 433/174; 433/173
[58] Field of Search ............... 433/173, 174, 175, 176; 606/65

[56] References Cited

U.S. PATENT DOCUMENTS

| | | | |
|---|---|---|---|
| 4,468,200 | 8/1984 | Munch | 433/174 |
| 4,863,383 | 9/1989 | Grafelmann | 433/174 |
| 5,000,686 | 3/1991 | Lazzara et al. | 433/174 |
| 5,078,607 | 1/1992 | Niznick | 433/174 |
| 5,195,892 | 3/1993 | Gersberg | 433/173 |
| 5,205,745 | 4/1993 | Kamuja et al. | 433/174 |

FOREIGN PATENT DOCUMENTS

| | | | |
|---|---|---|---|
| 4096745 | 3/1992 | Japan | 433/174 |
| 3012733 | 7/1993 | WIPO | 433/174 |

Primary Examiner—Cary E. O'Connor
Attorney, Agent, or Firm—Morton J. Rosenberg; David I. Klein

[57] ABSTRACT

An endosseous dental implant system comprises a root formed, mechanically retained base and an intimate, inter-locking threaded coronal attachment. The root formed base is comprised of a self-locking, externally threaded, tapered shell, and an anti-rotational internally threaded, countersunk plug which is permanently attached below the coronal surface of the shell, thus forming a single unit. Internally, the coronal portion of the shell has a downward tapered bevel for locking the anti-rotational coronal attachment to the base once attached via the internal threads of the permanently connected countersunk plug. Self-tapping threads are incorporated into the apex of the root formed base for easy insertion and immediate locking with the osteotomy. Downward from the coronal portion through the midsection of the root formed base is a specially designed stress distributing thread for uniform loading through the implant site. Finally, to simulate the physiological conditions, the implant system is manufactured from a material that closely replicates the natural dentition.

15 Claims, 3 Drawing Sheets

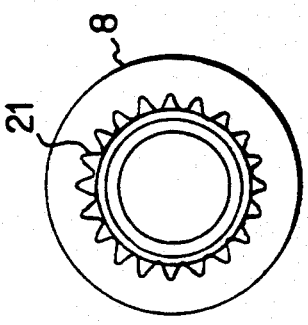
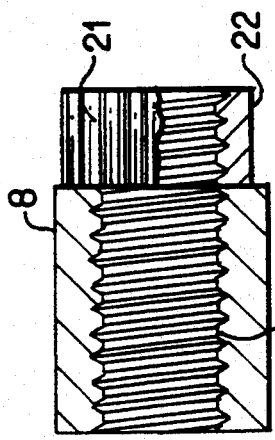
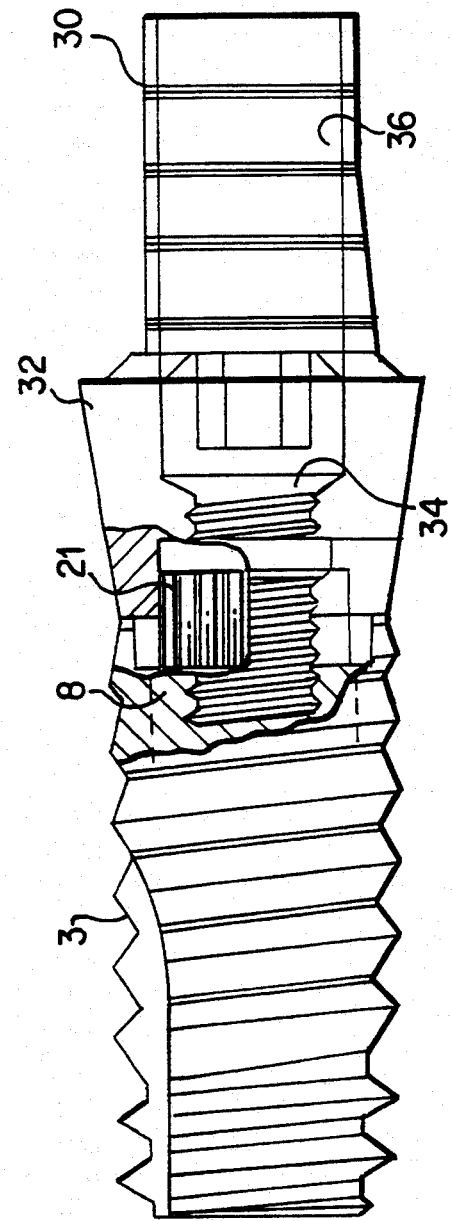

ENDOSSEOUS DENTAL IMPLANT SYSTEM

BACKGROUND OF THE INVENTION

1. Field of the Invention

The invention relates to artificial orthopaedic implant prosthesis, and particularly, but not exclusively, to dental implants.

2. Description of the Prior Art

Presently, dental implants to replicate the function of an extracted or lost tooth, do so by rigidly fixing a primarily metallic implant to a bone-implant site. Although these implants have provided the dental industry with a certain degree of success, the absence of the biomechanical periodontal ligament, which evenly distributes the occlusal loads to the entire implant site, has caused the bone to resorb over time in certain regions of the implant.

Over the last twenty-five years many root formed dental implants have been designed to replace natural dentition and provide for both aesthetic and functional occlusion. Although these designs provided for certain distinct mechanical characteristics for attaching the adjoining bone to the implant, they do not address the replacement and functional significance of the extracted periodontal ligament. Since the periodontal ligament acts as an intermediate barrier between the natural dentition and the osteodontic site (which absorbs and uniformly distributes the occlusal loads), the omission of such a feature can be devastating to an implant's success. Presently, many groove, thread, and hole implant designs are available to mechanically fixture and permanently lock the implant to the bone without any consideration for the structural loading to the implant site and the significance of the periodontal ligament.

In 1983, an attempt was made to provide an implant system that simulated the physiological function of the periodontal ligament by inserting an intermediate attachment between the coronal element and the artificial root made from an elastic polymer. Although, in principle the design provided for a method to absorb the normal occlusion, the design failed to uniformly distribute the stress to the underlying bone that the implant was attached to. Furthermore, due to the weak mechanical characteristics of the elastic material, failure of this intermediate component was inevitable.

Since then, many attempts have been made using computer aided finite element analysis to evaluate the stress distribution of various implant geometries in order to find the ideal design, assuming rigid fixation to the attached bone. Although this data has provided significant insight to the structural behavior of many geometries that exist today, few new practical designs using this technology have been developed due to their manufacturing and surgical requirements.

What is needed is a specific thread geometry to evenly distribute the occlusal loads throughout the entire length of the implant.

The object of my invention is to emulate, with a dental implant, the anatomical conditions of natural dentition using a defined geometry and unique material, that can be easily manufactured and surgically placed.

Another object of my invention is to provide the implant with an interlocking mechanism to drive and secure the implant into the jaw and act as a receptor for securing a prosthetic attachment.

It is further the object of my invention to uniformly distribute the stress throughout the entire length of the implant, and prevent bone loss, buy using a specially designed mechanically locking tapered thread.

These and other objects of my invention will be apparent from the following description taken with reference to the accompanying drawings.

BRIEF SUMMARY OF THE INVENTION

The endosseous dental implant comprises two separate components assembled and permanently linked together as a single unit. The two components consist of a specially designed externally threaded shell for a uniform distribution of stress to the implant site and an internally threaded anti-rotational plug for securing prosthetic attachments.

Over the past several years many attempts have been made to develop a stress shielding design. The current designs have not proven to be clinically successful. What is disclosed is a unique design which has never been published, machined or manufactured. It introduces a series of cones in alternating helical design over the first six millimeters of the implant body. These cones are of two basic mechanical designs. The first cone is large in surface area and is at an angle of incidence relative to a perpendicular to the long axis of the fixture which first introduces tension. The first cone is located at the top or coronal portion of the implant. Tension, being the inverse of compression, will provide a significant decrease in the vector force distributed into the bone. By increasing the angle of incidence and the volume of the surface area, this design transfers the majority of the initial stress to the second cone. The second cone is a cone of compression. This cone starts with a much lower angle of incidence which is compensated for by significantly reducing the volume of the cone. Stress introduced into the surrounding medium is a function of the combination of both angle of incidence and the amount of interface contact or combined surface area relative to the surrounding medium. By alternating cones of tension and compression over the next six millimeters of implant length in such a way to decrease the surface area and decrease the angle of incidence of tension cones, and increase the surface area and increase the angle of incidence of the compression cones, the design evenly distributes and diverts the stress over a larger volume thereby minimizing the initial incidence of trauma at the first point of contact. The design also allows for a decreasing diameter and gradual introduction of the anchor threads which maximizes the physical properties of the material.

This unique design and application will apply to all implant-bone interfaces in the dental and medical profession. This would include hips, knees, shoulders, and all orthopedic retaining prosthesis involving a bone-implant interface.

The invention may be better visualized by now turning to following drawings wherein like elements are referenced by like numerals.

BRIEF DESCRIPTION OF THE DRAWINGS

FIG. 3 is a cross-sectional drawing of the internally threaded countersunk plug of the endosseous implant prior to assembly.

FIG. 4 is a partially cutaway side view of the assembled implant showing the shell, plug and post in combination.

FIG. 5 is a top plan view of the plug of FIG. 3.

The invention may now be better understood by turning to the following detailed description.

DETAILED DESCRIPTION OF THE PREFERRED EMBODIMENTS

The invention will be described by using specific language with reference to the accompanied illustrated embodiments. However, it is understood that the scope of the invention includes any modifications or alterations which would be obvious to anyone skilled in the art to which my invention relates. Designated numbers will be used to describe each component in the preferred embodiment.

An endosseous dental implant system comprises a root formed, mechanically retained base and an intimate, inter-locking threaded coronal attachment. The root formed base is comprised of a self-locking, externally threaded, tapered shell, and an anti-rotational internally threaded, countersunk plug which is permanently attached below the coronal surface of the shell, thus forming a single unit. Internally, the coronal portion of the shell has a downward tapered bevel for locking the anti-rotational coronal attachment to the base once attached via the internal threads of the permanently connected countersunk plug. Self-tapping threads are incorporated into the apex of the root formed base for easy insertion and immediate locking with the osteotomy. Downward from the coronal portion through the midsection of the root formed base is a specially designed stress distributing thread for uniform loading through the implant site. Finally, to simulate the physiological conditions, the implant system is manufactured from a material that closely replicates the natural dentition.

Figure 1:
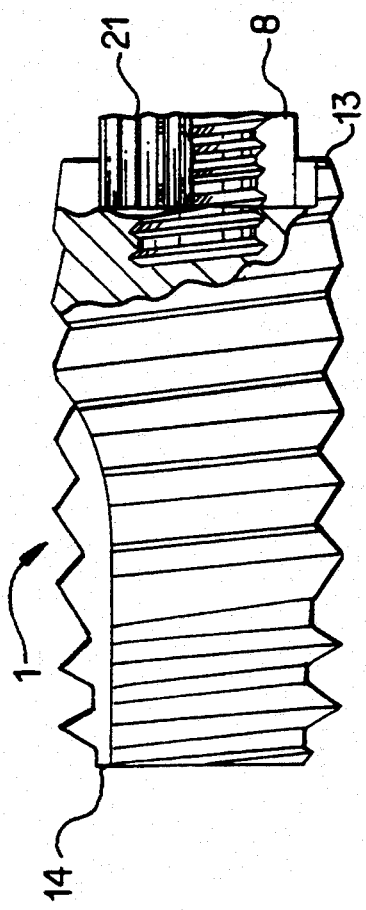
FIG. 1 is a partially cutaway side view of the endosseous dental implant with its plug installed prior to assembly with the tooth post.

As shown in FIG. 1 the endosseous dental implant 1, according to my present invention, is comprised of a self-locking externally threaded tapered shell 3 which is used to self-tap the root formed implant 1 into a pre-fabricated implant site in the bone. Interposed and a permanently attached within the shell 3 is an internally threaded, countersunk plug 8 that acts as a host for all the coronal attachments. These two unique components, the externally threaded taper shell 3 and the internally threaded countersunk plug 8, are permanently attached below the coronal portion of shell 3 forming a single unit 1 by means of a welding process. By countersinking threaded plug 8 below the upper ridge of the implant shell 3 certain desired features can be provided to the implant, without increasing the overall height of the prosthetic attachments.

Figure 2:
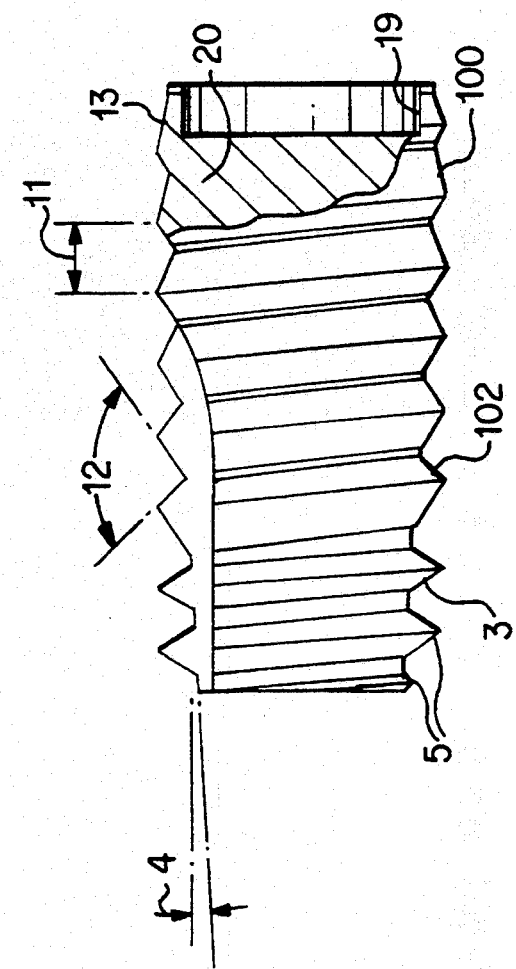
FIG. 2 is a partially cutaway side view of the externally threaded tapered shell of the endosseous implant prior to assembly with any other elements.

The disclosed geometry evenly distributes the occlusal loads throughout the entire length of the implant. As depicted in FIG. 2, since the applied occlusal stress is highest in the coronal aspect of the implant, the implant geometry incorporates a functional thread pitch 11 and thread angle 12 to allow for a uniform load distribution throughout the entire length of the implant. The geometry progressively increases the stress axially from the coronal portion to the apex 14 or bottom end of the implant site by simultaneously tapering the minor diameter of the thread inward by an angle 4 while increasing the angle of the thread angle 12. See the difference in thread angle between positions 100 and 102. Changing these parameters, the thread's minor diameter and the thread's angle 12, allows for reduced compression and maximize the tension at the top of implant 1 and then gradually converts these structural characteristic downward to generate a uniform stress field in the implant site.

Incorporated at the apex of the implant is a self-tapping thread 5 to pull the implant downward during its initial placement. To assist in this process and to lock the implant into place, the thread 5 will utilize a specially designed cutting flute to cut, form, and lock the implant into place.

At the coronal end 13 of the externally threaded shell 3 are two internally tapered countersunk bores 19 and 20. Bores 19 and 20 incorporate self-locking tapers to snugly attach their respective corresponding mating male elements described below. Of these two bores uppermost bore 19 is used as a receptor for attaching all prosthetic components, while lower bore 20 will be used for fixing the implant's internally threaded countersunk plug 8.

As seen in FIG. 1, assembled and permanently attached to the coronal portion 13 of the externally threaded shell 3 is the internally threaded countersunk plug 8. Plug 8, prior to assembly as seen in FIG. 3, is comprised of an anti-rotational locking spline 21 at the coronal end 22 of the plug 8, and a tapped internal thread 7 defined throughout the entire length of a tapered bore 9. The assembly of plug 8 requires that the locking spline 21, for structural advantages, be recessed below internally tapered bore 19 of externally threaded shell 3. Once assembled and permanently attached to shell 3 via a welding process, coronal end 22 of the countersunk plug 8 is used for driving the implant into its pre-fabricated implant receptor site in the bone and provides a means of locking to mating prosthetic attachments.

These aforementioned components, externally threaded bone locking tapered shell 3 and the internally threaded prosthetic securing countersunk plug 8, are assembled and permanently attached to each other to achieve the previously stated objects in a functional and manufacturable manner. The assembled implant is shown in partial cutaway side view in FIG. 4. Plug 8 is fixed by welding, gluing or other means into shell 3. An abutment 32 is then aligned onto splines 21 on plug 8 as best shown in the top plan view of FIG. 5 of plug 8. Abutment 32 extends to integrally or separably provide a post 30 to which the tooth or prosthetic (not shown) is attached by conventional means. Conforming splines are defined internally in the mating end of abutment 32. Abutment 32 is then secured to plug 8 by means of a stainless steel socket-hex head bolt 34 disposed within bore 36 of post 30 and abutment 32. Bolt 34 screws into threading 7 defined in bore 9 of plug 8. Post 30 or the prosthetics attached to post 30 may be custom molded and angled to conform to the specific bite of each patient according to conventional dental lab techniques.

Figure 8:
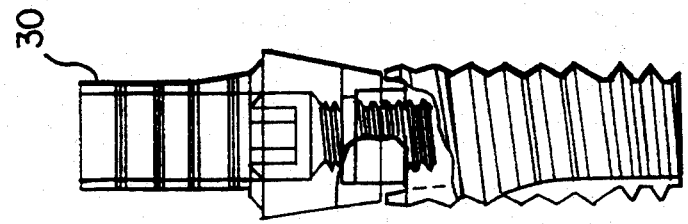
Figure 6:
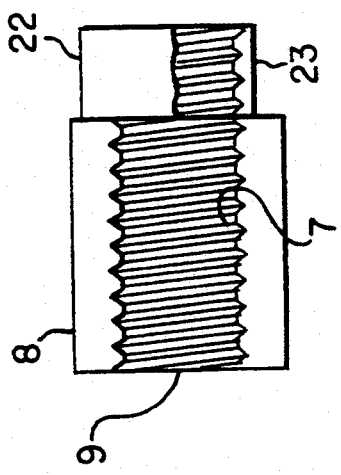
FIG. 6 is a cross-sectional side view of a second embodiment of the plug utilizing a flat instead of a spline connection for alignment of the post.
Figure 7:
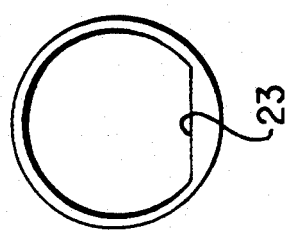
FIG. 7 is a top plan view of the plug of FIG. 6.

A second embodiment of the invention is depicted in FIGS. 7 and 8. In the second embodiment internally threaded countersunk plug 8 alters the connection between the abutment and implant 1 described above to address a very common problem in implant dentistry that has had no prior solution. Modified plug 8 comprises a straight slot taperlock connection which is machined on a one degree thirty minutes Mores taper to cold weld plug 8 to the shell 3 in only one position. The position is fixed by means of a flat 23 defined on end 22 of plug 8. A corresponding flat is then defined internally on abutment 32 in place of splines 21 used in the embodiment of FIGS. 1-5.

Prior art implants have had various types of structures to provide multiple reproducible locations to accommodate an angled fixture or post. This has created a clinical problem of relocating plug 8 in the oral cavity from the working model at the time of insertion of plug 8 and the final prosthesis. This complication leads to remakes and multiple appointments. By designing the connection to only fit in one direction this assures accurate repositioning and reproducible transfer during clinical procedures.

An external cylinder is machined to a Mores Taper at one degree thirty minutes to secure the abutment during final seating. Angled fixtures or posts will be accommodated by casting to the post 30 shown in FIG. 8. The feature of the external cylinder with a straight slot or flat also solves the difficult manufacturing issue of creating a reproducible Mores taper in a hex or octagon design which has been unsuccessfully attempted by prior art manufacturers.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. The following claims are, therefore, to be read to include not only the combination of elements which are literally set forth, but all equivalent elements for performing substantially the same function in substantially the same way to obtain substantially the same result. The claims are thus to be understood to include what is specifically illustrated and described above, what is conceptionally equivalent, and also what essentially incorporates the essential idea of the invention.

I claim:

1. An endosseous dental implant for implanting into bone comprising:
   a fixture having a elongate shape along a longitudinal axis;
   an implant body;
   a first series of cones in helical pattern provided over the first portion of said implant body, said first series of cones having a large surface area and an angle of incidence relative to a perpendicular to said longitudinal axis of said fixture to introduce tension, said cones being defined as tension cones, said first series of cones being located at a coronal portion of said implant, said tension providing a significant decrease in the vector force distributed into said bone; and
   a second series of cones with a lower angle of incidence than said first series of cones and a reduced the volume of said cones compared to said first series of cones to transfer the majority of said stress to said second series of cones, said second series of cones to produce compression and being defined as compression cones,
   whereby stress is evenly distributed and diverted over a larger volume thereby minimizing the initial incidence of trauma at the first point of contact.

2. The implant of claim 1 wherein said first and second series of cones are alternated to provide cones of tension and compression over a selected portion of said implant length to decrease the surface area and decrease the angle of incidence of said tension cones, and increase the surface area and increase the angle of incidence of the compression cones.

3. The implant of claim 1 wherein said implant has a decreasing diameter toward its bottom and comprises anchor threads gradually defined in its lower portion.

4. An endosseous dental implant for disposition in an implant for disposition in an implant site comprising:
   a longitudinally extended shell having a longitudinally directed bore formed in one end thereof and a screw-type thread helically formed on an external surface thereof, said helical screw-type thread being defined by threads having at least two different thread angles for providing a uniform distribution of stress to the implant site; and
   an internally threaded anti-rotational plug disposed within said bore of said shell and affixed to said shell for securing prosthetic attachments.

5. The implant of claim 4 further comprising an abutment for affixation to said plug wherein said plug is rotationally fixed to said abutment by splines 6. The implant of claim 4 further comprising an abutment for affixation to said plug wherein said plug is rotationally fixed to said abutment by a flat defined in said plug and abutment.

7. The implant of claim 4 wherein said helical screw-type thread includes:
   a first series of cones disposed in a helical pattern provided over a first portion of said external surface of said shell, said first series of cones having a large surface area and an angle of incidence relative to a perpendicular to said longitudinal direction of said shell to introduce tension, said cones being defined as tension cones, said first series of cones being located at a coronal portion of said shell, said tension providing a significant decrease in a vector force distributed into said implant site; and
   a second series of cones with a lower angle of incidence than said first series of cones and a reduced the volume of said second series of cones compared to said first series of cones to transfer a majority of said stress to said second series of cones, said second series of cones producing compression and being defined as compression cones.

8. The implant of claim 7 wherein said first and second series of cones are alternated to provide cones of tension and compression over a selected portion of said implant length to decrease the surface area and decrease the angle of incidence of said tension cones, and increase the surface area and increase the angle of incidence of the compression cones.

9. The implant of claim 8 wherein said implant has a decreasing diameter toward its bottom and comprises anchor threads gradually defined in its lower portion.

10. The implant of claim 4 wherein said plug is disposed within said bore of said shell with a main body portion of said plug disposed below an upper ridge of said shell.

11. The implant of claim 4 wherein said plug is affixed within said bore of said shell by welding.

12. The implant of claim 11 further comprising an abutment secured to a coronal end of said plug.

13. The implant of claim 12 wherein said plug is disposed within said bore of said shell with a main body portion of said plug disposed below an upper ridge of said shell to form an annular recess for receiving a portion of said abutment therein.

14. The implant of claim 4 wherein said plug has an external surface contour defined by a predetermined taper for forming a taperlock connection with said shell.

15. The implant of claim 4 wherein said shell further includes a self-tapping thread formed on said external surface thereof adjacent a distal end of said shell.

* * * * *